(12) United States Patent
Tamaki

(10) Patent No.: US 11,160,965 B2
(45) Date of Patent: Nov. 2, 2021

(54) METHOD FOR MANUFACTURING TRANSDERMAL ABSORPTION SHEET

(71) Applicant: FUJIFILM Corporation, Tokyo (JP)

(72) Inventor: Kenichiro Tamaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/202,360

(22) Filed: Mar. 16, 2021

(65) Prior Publication Data

US 2021/0196938 A1 Jul. 1, 2021

Related U.S. Application Data

(63) Continuation of application No. PCT/JP2019/037478, filed on Sep. 25, 2019.

(30) Foreign Application Priority Data

Sep. 26, 2018 (JP) .............................. JP2018-180246

(51) Int. Cl.
*A61M 37/00* (2006.01)
*B29C 43/36* (2006.01)
*B29C 43/56* (2006.01)

(52) U.S. Cl.
CPC ......... *A61M 37/0015* (2013.01); *B29C 43/36* (2013.01); *B29C 43/56* (2013.01);
(Continued)

(58) Field of Classification Search
CPC .......... A61M 37/0015; A61M 2207/00; A61M 2037/0053; A61M 2037/0023;
(Continued)

(56) References Cited

U.S. PATENT DOCUMENTS

2017/0361082 A1 12/2017 Okano et al.

FOREIGN PATENT DOCUMENTS

JP 2009241358 10/2009
JP 2009241358 A * 10/2009
(Continued)

OTHER PUBLICATIONS

"International Search Report (Form PCT/ISA/210) of PCT/JP2019/037478," dated Dec. 10, 2019, with English translation thereof, pp. 1-4.
(Continued)

*Primary Examiner* — Amber R Stiles
(74) *Attorney, Agent, or Firm* — JCIPRNET

(57) ABSTRACT

Provided is a method for manufacturing a transdermal absorption sheet which makes it possible to manufacture a transdermal absorption sheet with a stable shape. The method for manufacturing a transdermal absorption sheet includes a step of forming a drug layer (110) on needle-like recess portions (42) of a mold (50) having the needle-like recess portions (42), a step of supplying a polymer layer forming solution (112) to the inside of a step portion (52) of the mold (50), a step of drying the polymer layer forming solution (112) so as to form a polymer layer (114) and a transdermal absorption sheet (120), and a step of peeling off the transdermal absorption sheet (120) from the mold (50). In the step of peeling off, pressing force is applied to a part of the step portion (52) in a second direction (B) opposite to a first direction (A) in which the transdermal absorption sheet (120) is released from the mold (50), and the transdermal absorption sheet (120) is aspirated with a vacuum suction pad (160) from a side opposite to the mold (50) so that the transdermal absorption sheet (120) is peeled off from the mold (50) in the first direction (A).

7 Claims, 10 Drawing Sheets

(52) U.S. Cl.
CPC ............ *A61M 2037/0023* (2013.01); *A61M 2037/0053* (2013.01); *A61M 2207/00* (2013.01); *B29C 2043/3605* (2013.01); *B29C 2043/561* (2013.01)

(58) Field of Classification Search
CPC ... B29C 43/56; B29C 43/36; B29C 2043/561; B29C 2043/3605
See application file for complete search history.

(56) References Cited

FOREIGN PATENT DOCUMENTS

| | | | | |
|---|---|---|---|---|
| JP | 2010234669 | | 10/2010 | |
| JP | 2016168325 | | 9/2016 | |
| JP | 2016168325 | A * | 9/2016 | ........... B29C 39/025 |

OTHER PUBLICATIONS

"Written Opinion of the International Searching Authority (Form PCT/ISA/237) of PCT/JP2019/037478," dated Dec. 10, 2019, with English translation thereof, pp. 1-10.

* cited by examiner

METHOD FOR MANUFACTURING TRANSDERMAL ABSORPTION SHEET

CROSS-REFERENCE TO RELATED APPLICATIONS

The present application is a Continuation of PCT International Application No. PCT/JP2019/037478 filed on Sep. 25, 2019 claiming priority under 35 U.S.C § 119(a) to Japanese Patent Application No. 2018-180246 filed on Sep. 26, 2018. Each of the above applications is hereby expressly incorporated by reference, in its entirety, into the present application.

BACKGROUND OF THE INVENTION

1. Field of the Invention

The present invention relates to a method for manufacturing a transdermal absorption sheet, particularly, to a method for manufacturing a transdermal absorption sheet by shape transfer using a mold in which needle-like recess portions are formed.

2. Description of the Related Art

In recent years, a micro-needle array has been known as a novel dosage form capable of intradermally administering drugs such as insulin, vaccines, and human growth hormone (hGH) without pain. The micro-needle array is an array of biodegradable microneedles (also called fine needles) containing a drug. In a case where the micro-needle array is attached to the skin, the microneedles pierce and are absorbed into the skin, and hence the drug contained in the microneedles can be administered into the skin. The micro-needle array is also called a transdermal absorption sheet.

In order to prepare a molded article having a fine protrusion-like pattern such as the aforementioned micro-needle array, from a master having a fine protrusion-like pattern, a resinous mold is formed which has the shape of the master inverted, and then the molded article is prepared from the mold. There is a demand for improving the productivity of the molded article having such a fine pattern, and various methods have been suggested to satisfy the demand.

For example, JP2009-241358A describes a method for manufacturing a needle sheet, in which in a process of peeling off a needle sheet from a stamper, the entire circumference of a frame placed on the stamper is pressed down, so that fixing force acting in the opposite direction of the peeling force is applied, the stamper and the needle sheet are bent, and the needle sheet can be appropriately peeled off from a mold.

SUMMARY OF THE INVENTION

In the method described in JP2009-241358A, because fixing force acting in the opposite direction of the peeling force is applied to the entire circumference of the frame, it is difficult to sufficiently bend the stamper. Moreover, in order to peel off the needle sheet, the needle sheet to be manufactured is also bent. Therefore, sometimes the needle portion is damaged or the manufactured needle sheet is deformed, and a needle sheet having a stable shape cannot be manufactured.

Furthermore, in view of the mass production of a transdermal absorption sheet, it is desired that the transdermal absorption sheet can be mechanically and automatically released from a mold.

The present invention has been made in consideration of the above circumstances, and an object thereof is to provide a method for manufacturing a transdermal absorption sheet that inhibits needle-like protrusion portions and a transdermal absorption sheet from being damaged during peeling and makes it possible to manufacture a transdermal absorption sheet in a stable shape.

In order to achieve the object of the present invention, the method for manufacturing a transdermal absorption sheet according to an aspect of the present invention has a step of filling needle-like recess portions of a mold, which comprises the needle-like recess portions and a step portion that is formed around a region where the needle-like recess portions are formed and is higher than the region, with a drug solution and drying the drug solution so as to form a drug layer, a step of supplying a polymer layer forming solution to the inside of the step portion, a step of drying the polymer layer forming solution so as to form a polymer layer and a transdermal absorption sheet, and a step of peeling off the transdermal absorption sheet from the mold, in which in the step of peeling off, pressing force is applied to a part of the step portion in a second direction opposite to a first direction in which the transdermal absorption sheet is released from the mold, and the transdermal absorption sheet is aspirated by a vacuum suction pad from a side opposite to the mold so that the transdermal absorption sheet is peeled off from the mold in the first direction.

According to the method for manufacturing a transdermal absorption sheet according to the aspect of the present invention, in the process of peeling off the transdermal absorption sheet from the mold, pressing force is applied to a part of the step portion in the second direction opposite to the first direction in which the transdermal absorption sheet is released from the mold. In this state, the transdermal absorption sheet is aspirated in the first direction by a vacuum suction pad. As a result, the end portion of the mold is pushed in the second direction while the central portion thereof is pulled in the first direction, which enables the mold to bend. Because the pressing force is applied to a part of the step portion of the mold, the mold can be easily deformed. Accordingly, by aspirating the transdermal absorption sheet with a vacuum suction pad, it is possible to inhibit the damage of the needle-like protrusion portions and the deformation of the transdermal absorption sheet and to manufacture a transdermal absorption sheet in a stable shape.

DESCRIPTION OF THE PREFERRED EMBODIMENTS

Figure 1:
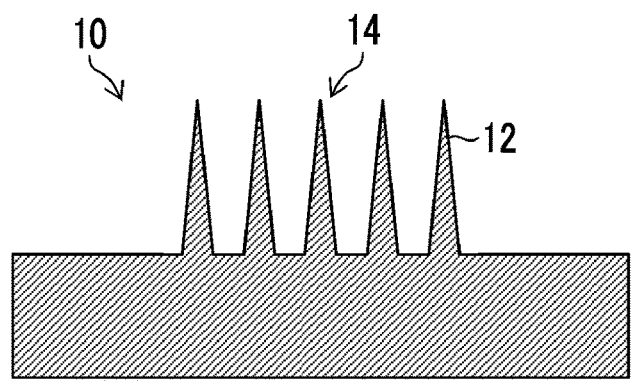
FIG. 1 is a process chart showing a procedure for manufacturing a mold.

Hereinafter, a method for manufacturing a transdermal absorption sheet according to an embodiment of the present invention will be described with reference to the attached drawings. In the present specification, "to" is used to show that the numerical values listed before and after "to" are the lower limit and the upper limit.

<Mold>

[Method for Manufacturing Mold]

FIGS. 1 to 5 are process charts showing the procedure of a method for manufacturing a mold. For manufacturing a mold 50, by performing imprinting on a resin matrix, a first mold 20 is formed from a master 10. After the first mold 20 is formed, a replication mold 30 is formed by an electroforming process. Then, by using a resin film, from the replication mold 30, a mold sheet 40 is formed which is in the form of an inverted replication mold 30 and includes needle-like recess portions 42. Finally, the mold sheet 40 is punched and cut for each pattern, thereby forming the mold 50. Hereinafter, each step will be described.

First, the master 10 shown in FIG. 1 is prepared, in which a protrusion-like pattern 14 consisting of an array of a plurality of needle-like protrusion portions 12 is formed. There is no particular limitation on the method for preparing the master 10 in which the protrusion-like pattern 14 is formed. For example, by processing a metal substrate such as stainless steel by means of mechanical cutting using a cutting tool such as a ball end mill, the plurality of needle-like protrusion portions 12 can be formed on the surface of the master 10.

As another method, a Si substrate is coated with a photoresist and then subjected to exposure and development. Then, the substrate is etched by reactive ion etching (RIE) or the like so that the needle-like protrusion portions 12 are formed on the surface of the master 10. In a case where etching such as RIE is performed to form the needle-like protrusion portions 12 on the surface of the master 10, by obliquely etching the Si substrate in a state of rotating the substrate, it is possible to form the needle-like protrusion portions 12.

Figure 2:
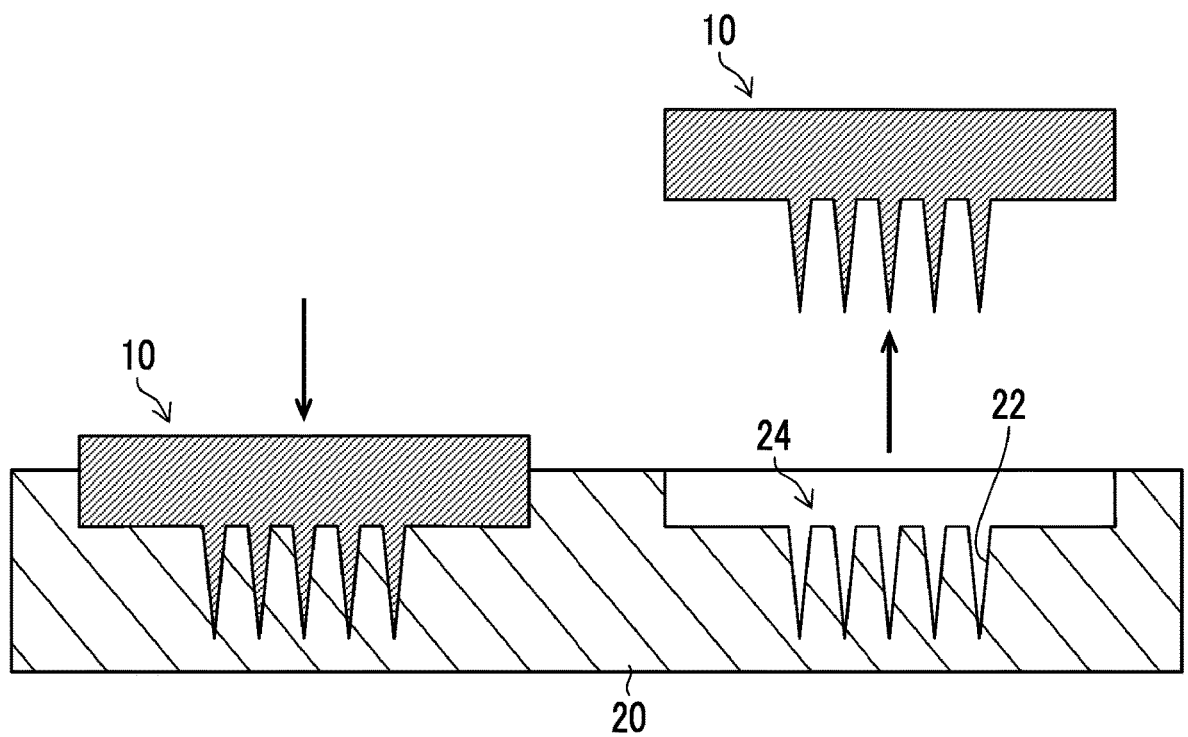
FIG. 2 is a process chart showing the procedure for manufacturing a mold.

Thereafter, as shown in FIG. 2, by using the master 10, a first mold 20 having a recess-like pattern 24 consisting of a plurality of needle-like recess portions 22 is prepared by an imprinting method. As a method for preparing the first mold 20, a resin matrix composed of the material of the first mold 20 such as a thermoplastic resin is prepared. The heated master 10 is pressed on the surface of the resin matrix, and the resin matrix is cured by cooling or the like, thereby forming the needle-like recess portions 22 on the surface of the resin matrix. Subsequently, the master 10 is peeled off from the resin matrix, and the resin matrix is molded as necessary. In this way, the first mold 20 can be manufactured. FIG. 2 shows the procedure of forming two recess-like patterns 24 having the needle-like recess portions 22 by using the master 10. However, the number of recess-like patterns is not limited. A first mold in which three or more recess-like patterns are formed may be manufactured.

Figure 3:
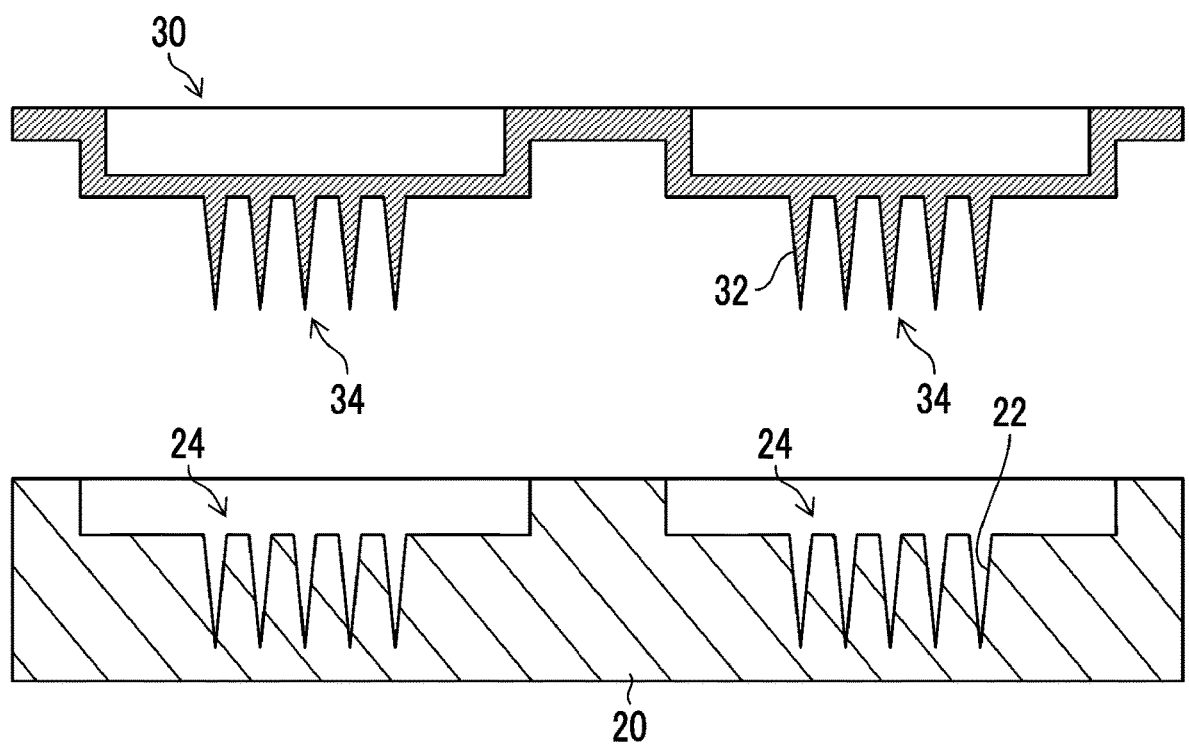
FIG. 3 is a process chart showing the procedure for manufacturing a mold.

Thereafter, as shown in FIG. 3, by using the first mold 20, the replication mold 30 having a protrusion-like pattern 34 consisting of needle-like protrusion portions 32 is prepared. It is preferable that the replication mold 30 be prepared by an electroforming process.

In the electroforming process, first, the first mold 20 is processed to have conductivity. A metal (for example, nickel) is deposited onto the first mold 20 by sputtering. In this way, the metal is attached to the surface of the first mold 20 and the needle-like recess portions 22.

Then, the first mold 20 processed to have conductivity is held in a cathode. Metal pellets are held in a metal case and used as an anode. The cathode holding the first mold 20 and the anode holding the metal pellets are immersed in an electroforming solution, and electric currents are applied thereto, so that the metal is embedded in the needle-like recess portions 22 of the first mold 20. Then, the metal is peeled off, thereby preparing the replication mold 30 having protrusion-like pattern 34.

The electroforming process is not the only way of preparing the replication mold 30 having the protrusion-like pattern 34. The replication mold 30 can also be prepared by a method of supplying a resin to the first mold 20 and curing the resin. By dispersing metal particles in the supplied resin, the metal can be incorporated into the replication mold 30.

The steps shown in FIGS. 1 to 3 are not the only way of preparing the replication mold 30 having the protrusion-like pattern 34. For preparing the replication mold 30, it is also possible to use a mold (large-sized master) which is prepared by the same method as the method used for preparing the master 10 and in which a plurality of protrusion-like patterns is formed. However, it costs more to prepare a master having a finer and more complicated pattern shape. Therefore, preparing a large-sized master costs a lot of money. Furthermore, there is a concern that the needle-like protrusion portions may have different shapes. Therefore, in a case where the first mold 20 having a plurality of recess-like patterns is prepared from the master 10 by imprinting as shown in FIGS. 1 to 3, it is possible to prepare the mold with low costs.

Figure 4:
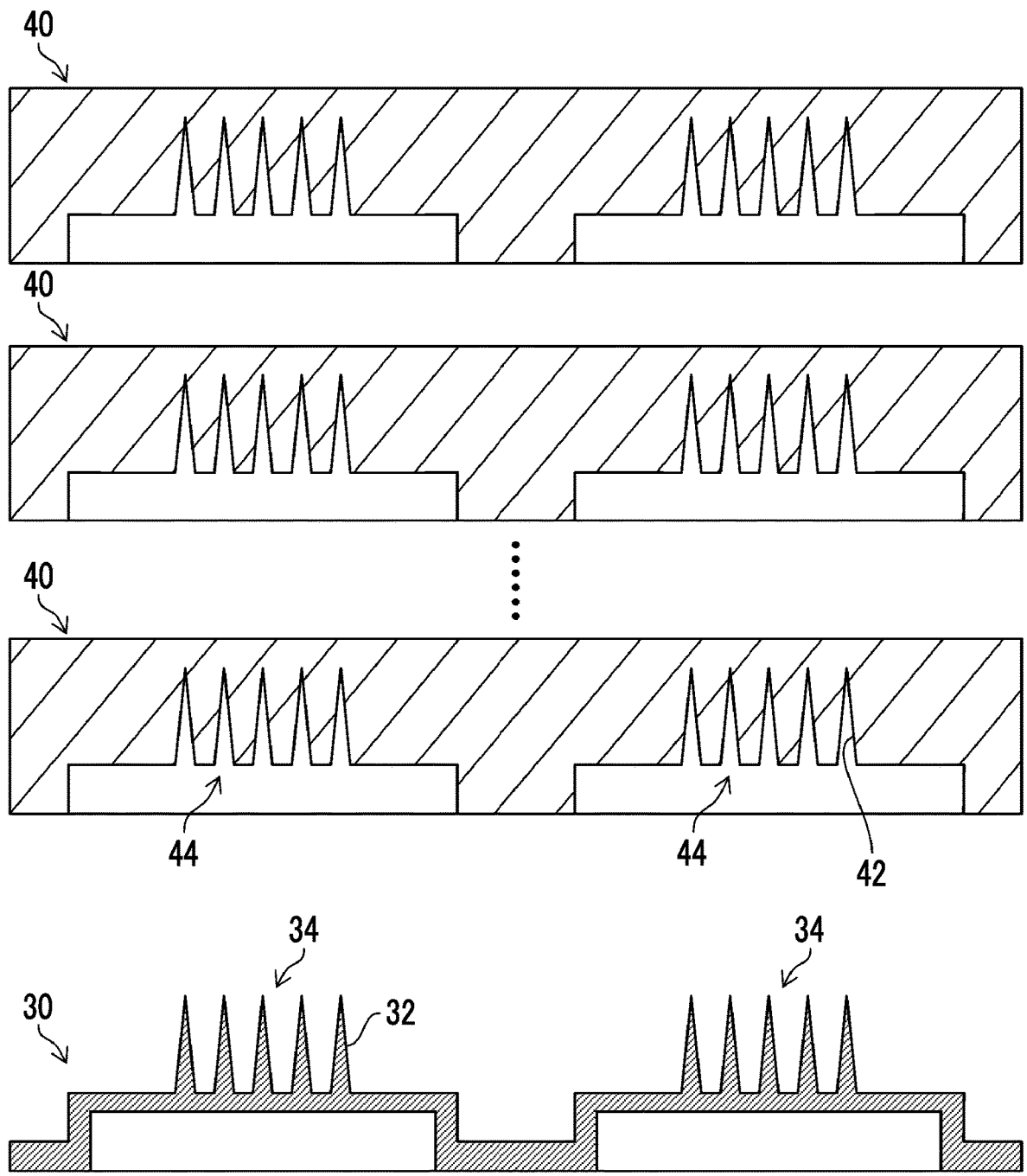
FIG. 4 is a process chart showing the procedure for manufacturing a mold.

Then, as shown in FIG. 4, a mold sheet 40 is manufactured using the replication mold 30. The mold sheet 40 can be manufactured by pouring a medical grade silicone material (for example, MDX4-4210 manufactured by Dow Corning) into the replication mold 30, heating the mold at 150° C. so that the material is cured, and then peeling off the mold sheet 40 from the replication mold 30. In addition, the mold sheet 40 can also be manufactured by a method of pouring a UV curable resin which is cured by being irradiating with ultraviolet rays into the replication mold 30, irradiating the resin with ultraviolet rays in a nitrogen atmosphere, and then peeling off the mold sheet 40 from the replication mold 30. Furthermore, the mold sheet 40 can also be manufactured by a method of pouring a solution obtained by dissolving plastic resins such as polystyrene and polymethylmethacrylate (PMMA) in an organic solvent into the replication mold 30 coated with a release agent, drying the solution so that the organic solvent is volatilized and the resins are cured, and then peeling off the mold sheet 40 from the replication mold 30. The formed protrusion-like pattern 34 of the replication mold 30 corresponds to a recess-like pattern 44 of the mold sheet 40.

Figure 5:
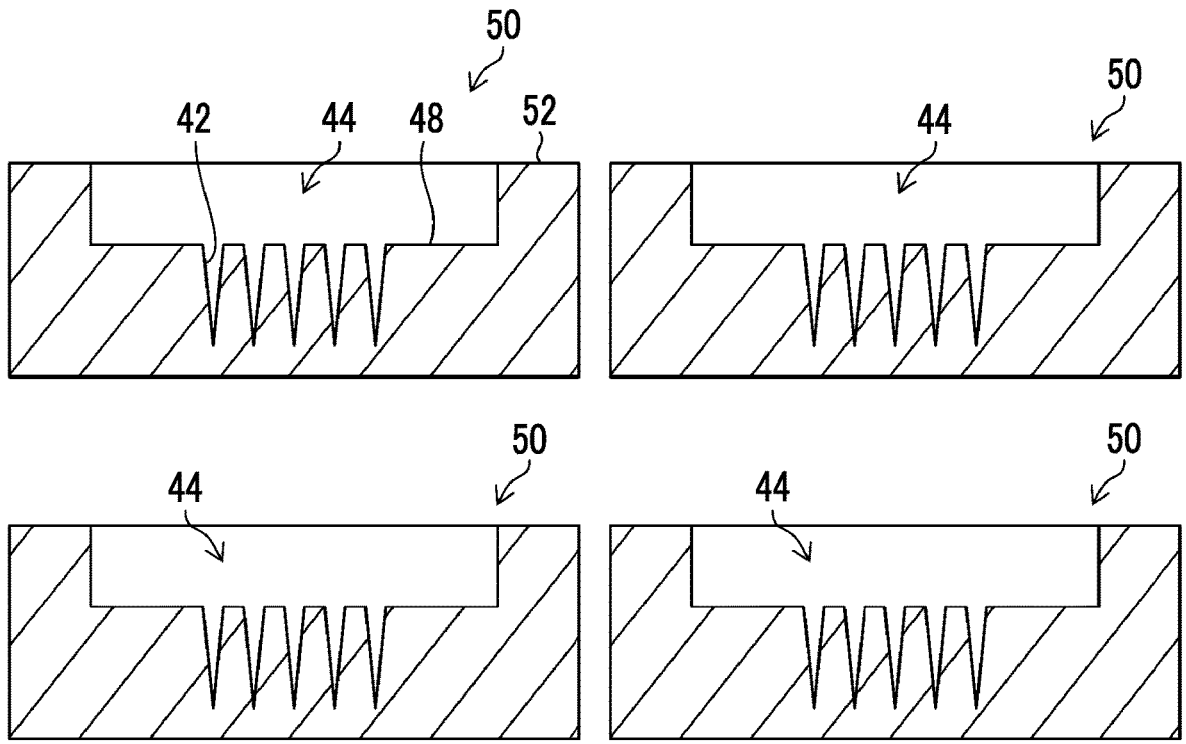
FIG. 5 is a process chart showing the procedure for manufacturing a mold.

Thereafter, as shown in FIG. 5, the mold sheet 40 is cut for each recess-like pattern 44 formed of needle-like recess portions 42, thereby manufacturing a mold 50. In this way, the mold 50 can be formed which is in the form of an inverted master 10 and has an array of a plurality of needle-like recess portions 42.

[Method for Manufacturing Transdermal Absorption Sheet]

Next, a method of manufacturing a transdermal absorption sheet using the mold 50 manufactured by the above manufacturing method will be described.

Figure 6:
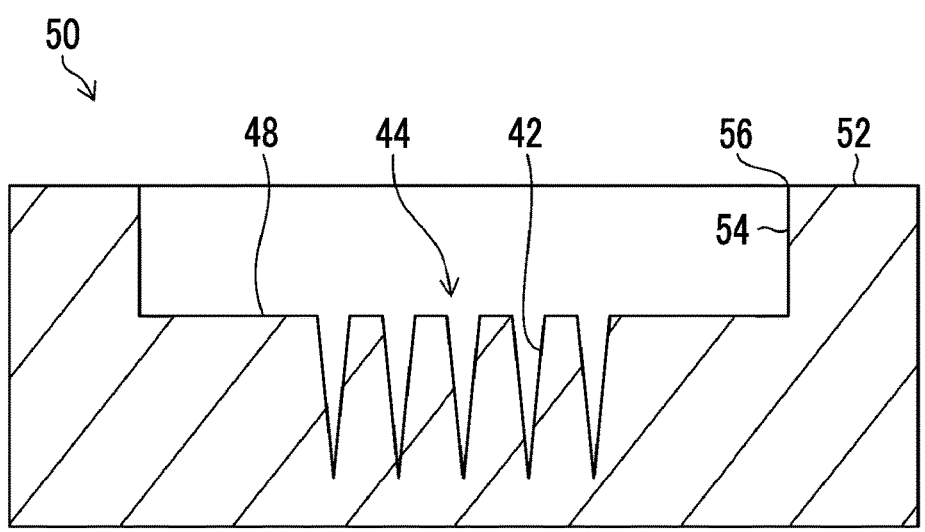
FIG. 6 is a process chart showing a procedure for manufacturing a transdermal absorption sheet.
Figure 7:
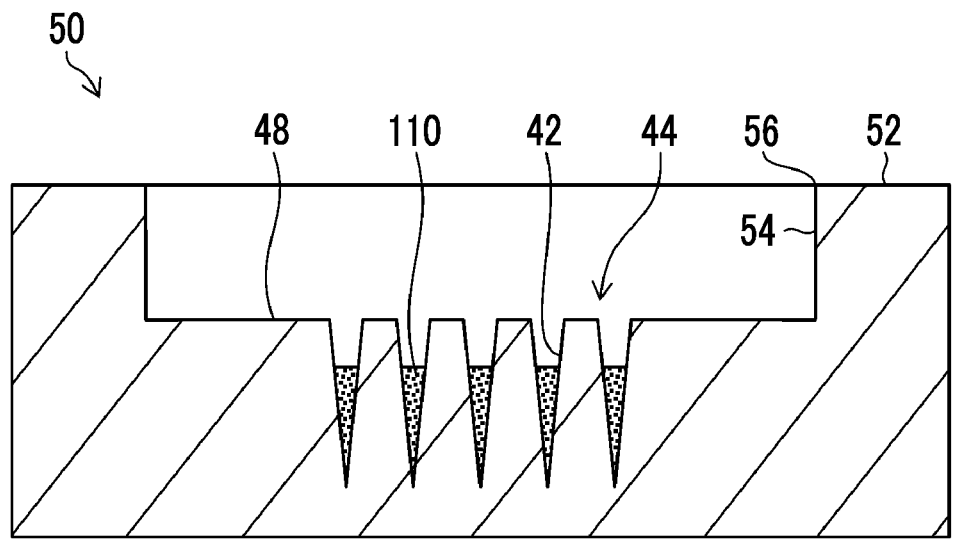
FIG. 7 is a process chart showing the procedure for manufacturing a transdermal absorption sheet.

First, the mold 50 is prepared as shown in FIG. 6. Then, as shown in FIG. 7, a drug solution is supplied to the needle-like recess portions 42 and dried, thereby forming a drug layer 110 in which the needle-like recess portions 42 contain the drug. To form the drug layer 110, a region 48 where the needle-like recess portions 42 are formed is coated with a drug solution containing a drug. The coating method is not particularly limited. For example, the drug solution can be supplied from a nozzle. Furthermore, a drop dispensing method may also be used. After being supplied, the drug solution can be aspirated from the back surface of the mold 50. In this way, it is possible to facilitate the filling of the needle-like recess portions 42 with the drug solution.

After the needle-like recess portions 42 are filled with the drug solution, the drug solution is dried to form the drug layer 110. In drying the drug solution, in a case where the drying rate is optimized by controlling the temperature and humidity conditions, it is possible to suppress the drug solution from sticking to the wall surface of the needle-like recess portions 42 and to cause the drug solution to dry while gathering at the tip of the needle-like recess portions 42.

By the drying, the drug solution is solidified and can contract further than the drug solution with which the needle-like recess portions 42 are filled. As a result, in the process of peeling off the transdermal absorption sheet 120 from the mold 50, the drug layer 110 can be easily peeled off from the needle-like recess portions 42.

Figure 8:
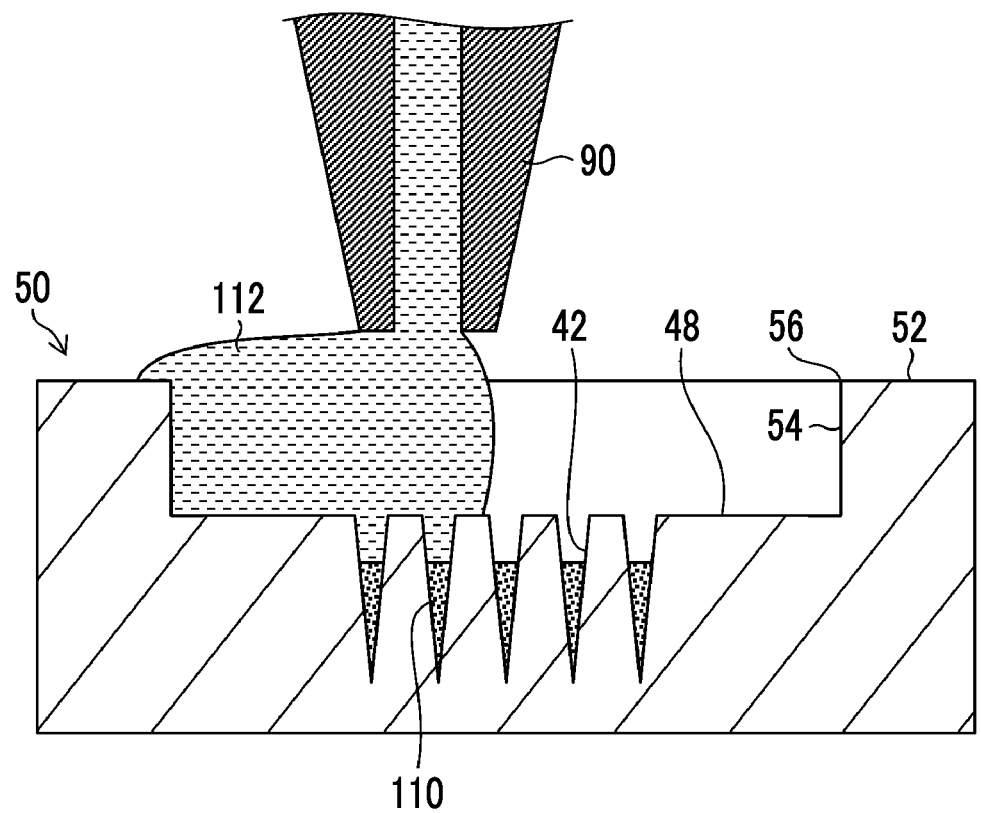
FIG. 8 is a process chart showing the procedure for manufacturing a transdermal absorption sheet.

Then, as shown in FIG. 8, a polymer layer forming solution 112 is supplied onto the drug layer 110 containing a predetermined amount of drug, so that the polymer layer forming solution 112 is supplied to the needle-like recess portions 42 and onto the region 48 where the needle-like recess portions 42 are formed. The polymer layer forming solution 112 is a polymer solution forming a polymer layer 114. To supply the polymer layer forming solution 112, it is possible to use coating by a dispenser, bar coating or spin coating, coating by spray or the like, coating by drop dispensing, and the like. However, the method of supplying the polymer layer forming solution 112 is not limited to these. The drug layer 110 is solidified by drying. Therefore, it is possible to inhibit the drug contained in the drug layer 110 from diffusing into the polymer layer forming solution 112.

Figure 9:
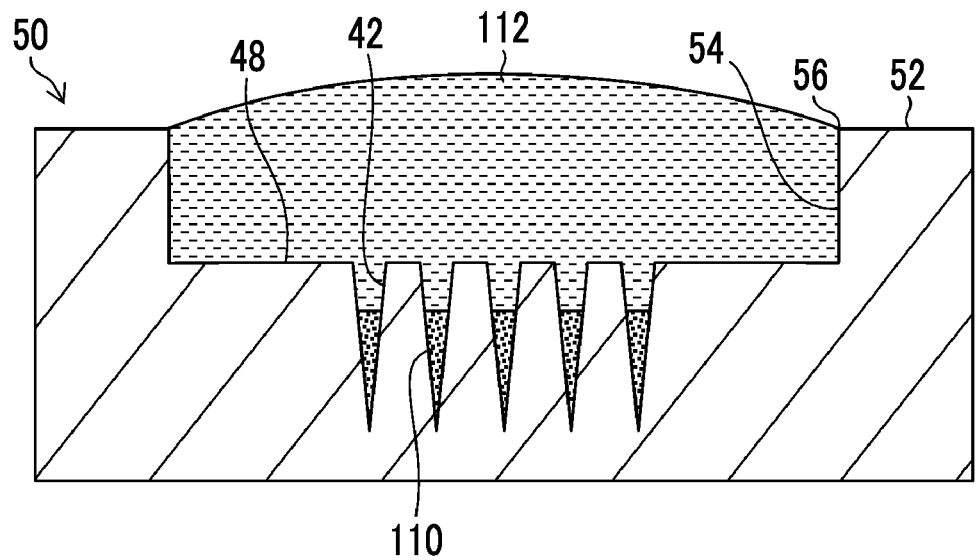
FIG. 9 is a process chart showing the procedure for manufacturing a transdermal absorption sheet.

During the supply of the polymer layer forming solution 112, as shown in FIG. 8, the polymer layer forming solution 112 is supplied by a supply unit 90, covers at least a part of a step portion 52 provided around the region 48 where the needle-like recess portions 42 are formed, and flows over a contact position 56 from the side of the region 48 where the needle-like recess portions 42 are formed. The supplied polymer layer forming solution 112 is repelled by the mold 50 and contracts due to surface tension. As shown in FIG. 9, the contracted polymer layer forming solution 112 is fixed (pinned) to the contact position 56 which is a point of contact between the step portion 52 of the mold 50 and a wall portion 54 extending to the step portion 52 from the region 48 where the needle-like recess portions 42 are formed. In a case where the polymer layer forming solution 112 is dried in a state of being fixed to the contact position 56, the polymer layer 114 of the transdermal absorption sheet can be stably shaped. Furthermore, before being dried, the polymer layer forming solution 112 may be aspirated from a side of the mold 50 that is opposite to the region 48 where the needle-like recess portions 42 are formed. By performing the aspiration, the needle-like recess portions 42 can be filled with the polymer layer forming solution 112. In addition, in a case where the polymer layer forming solution 112 has bubbles, it is possible to remove the bubbles by the aspiration.

Figure 10:
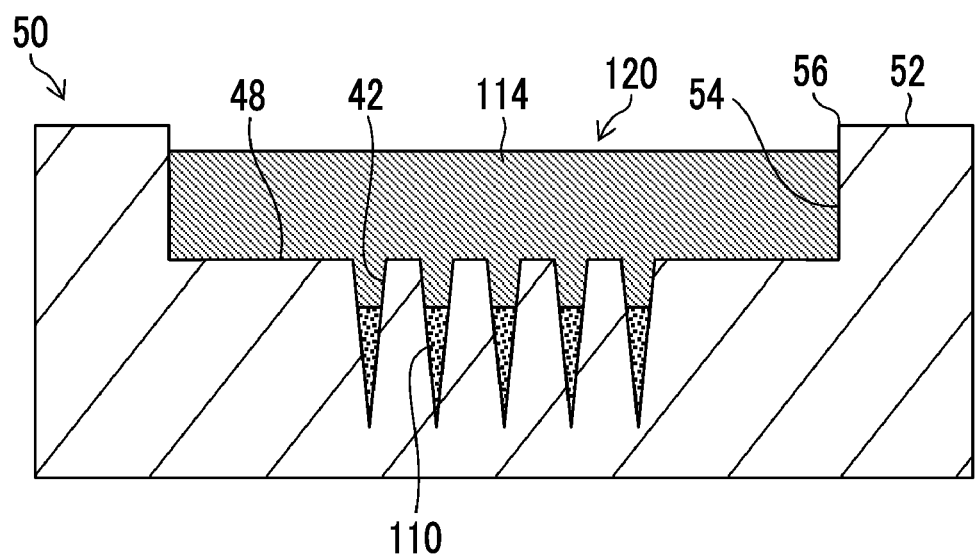
FIG. 10 is a process chart showing the procedure for manufacturing a transdermal absorption sheet.

After being supplied to the mold 50, the polymer layer forming solution 112 is dried and solidified. In this way, the polymer layer 114 can be formed on the drug layer 110 as shown in FIG. 10, and the transdermal absorption sheet 120 having the drug layer 110 and the polymer layer 114 can be manufactured.

The drying of the polymer layer forming solution 112 may be started in a state where the polymer layer forming solution 112 is fixed to the contact position 56 or in a state where the polymer layer forming solution 112 remains on the step portion 52. In a case where the drying is started in a state where the polymer layer forming solution 112 remains on the step portion 52, the polymer layer forming solution 112 on the step portion 52 is effectively rapidly dried. By the drying of the polymer layer forming solution 112 on the step portion 52, the polymer layer forming solution 112 can be fixed to the contact position 56.

As the polymer layer forming solution 112 dries, the volume of the polymer layer forming solution 112 is reduced. In a case where the polymer layer forming solution 112 is closely attached to the mold 50 during the drying, the volume is reduced in the film thickness direction of the sheet, which leads to the reduction in the film thickness.

The amount of water in the transdermal absorption sheet 120 after drying and the like are appropriately set. In a case where the amount of water in the polymer layer 114 is excessively reduced by drying, it is difficult to peel off the transdermal absorption sheet. Therefore, it is preferable to set the amount of water such that the transdermal absorption sheet retains elastic force.

Figure 11:
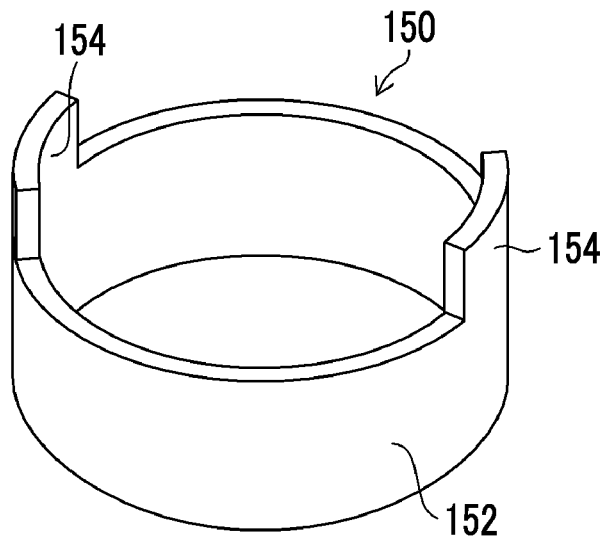
FIG. 11 is a perspective view of a pressing jig.
Figure 12:
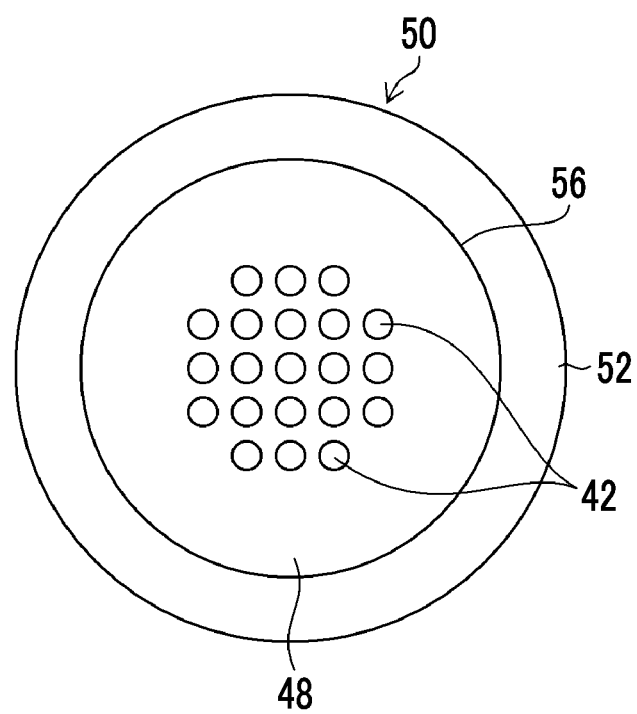
FIG. 12 is a plan view of a mold.

Then, the dried transdermal absorption sheet 120 is peeled off from the mold 50. In the process of peeling off the transdermal absorption sheet 120 from the mold 50, pressing force is applied to a part of the step portion 52. FIG. 11 is a perspective view of a pressing jig used for applying pressing force to the step portion 52. FIG. 12 is a plan view of the mold 50.

Figure 13:
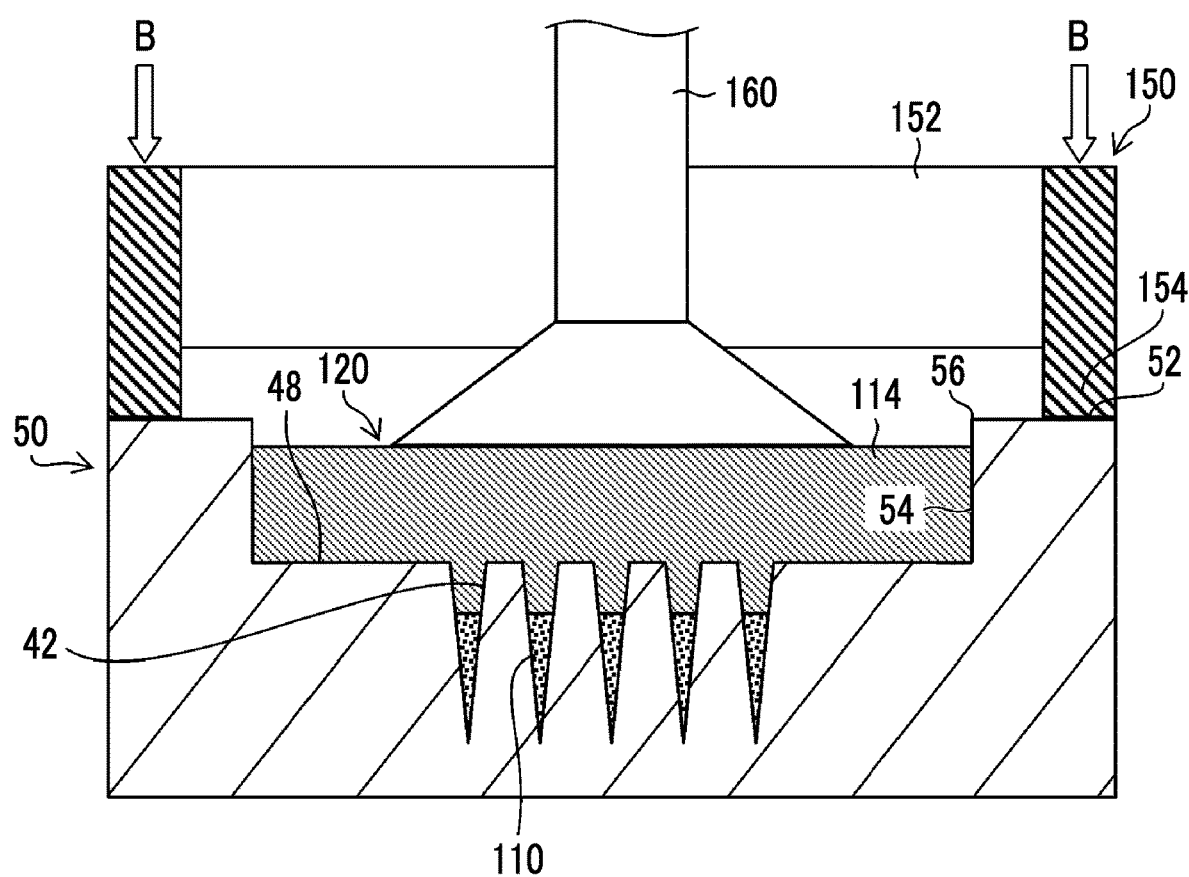
FIG. 13 is a process chart showing a procedure for peeling off a transdermal absorption sheet.

The pressing jig 150 shown in FIG. 11 is composed of a base portion 152 in the form of a hollow tube and claw portions 154 provided on the base portion 152. FIG. 13 is a view showing a state where the pressing jig is placed on the step portion, and pressing force is applied thereto. To apply the pressing force to the step portion 52, the pressing jig 150 is placed such that the claw portions 154 come into contact with the step portion 52. In FIG. 11, for a clear view of the claw portions 154 of the pressing jig 150, the claw portions 154 are on the upper side. However, the pressing jig 150 is inverted during use. As shown in FIG. 12, the mold 50 is in the form of a circle, and the step portion 52 is also in the form of a circle. By pressing the pressing jig 150, it is possible to apply pressing force to the step portion 52 at the position where the claw portions 154 come into contact with the step portion 52. By causing the pressing jig 150 to penetrate the base portion 152, it is possible to enable a vacuum suction pad 160 to pass through the base portion 152 in the process of aspirating the transdermal absorption sheet by the vacuum suction pad. In this way, the back surface side (opposite side of the mold 50) of the transdermal absorption sheet 120 can be aspirated by the vacuum suction pad 160.

The shape of the pressing jig 150 is not limited to the shape shown in FIG. 11. The shape of the pressing jig 150 is not particularly limited, as long as the jig 150 can press a part of the step portion 52, and the transdermal absorption sheet 120 can be aspirated from the back surface side thereof by the vacuum suction pad 160. Furthermore, the number of claw portions 154 is not limited to two as shown in FIG. 11, and a pressing jig having three or more claw portions can be used. However, the larger the number of claw portions 154 is, the less the mold 50 is deformed in a case where pressing force is applied to the step portion 52 by the pressing jig 150, and the harder it is to peel off the transdermal absorption sheet 120. Therefore, the increase in the number of claw portions 154 is not preferable. In addition, as long as the mold 50 can be fixed to a surface in contact with the mold and is not lifted together with the transdermal absorption sheet 120 in the process of releasing the transdermal absorption sheet 120 from the mold 50 by aspiration, the pressing jig 150 can have one claw portion. In the case of the pressing jig 150 shown in FIG. 11, the number of claw portions 154 is the number of positions at which the step portion 52 is pressed.

In a case where pressing force is applied to a plurality of sites of the step portion 52, it is preferable that the positions to which the pressing force is to be applied be arranged at equal intervals. In a case where the positions are arranged at equal intervals, the mold 50 can be evenly deformed, and the transdermal absorption sheet can be easily peeled off.

In the step portion 52, the proportion of the part to which pressing force is to be applied in the entire circumference of the step portion 52 is preferably equal to or lower than 75%, and more preferably equal to or lower than 50%. Furthermore, the proportion is preferably equal to or higher than 15%. In a case where the proportion of the part to which pressing force is to be applied is within the above range, it is possible to bend the mold 50 in the process of peeling off the transdermal absorption sheet. In addition, it is possible to prevent the mold 50 from being lifted up in the process of aspirating and peeling off the transdermal absorption sheet 120 by using the vacuum suction pad 160.

As the vacuum suction pad 160, in order to inhibit the deformation of the transdermal absorption sheet 120 during suction (aspiration), it is preferable to use a flat pad.

Figure 14:
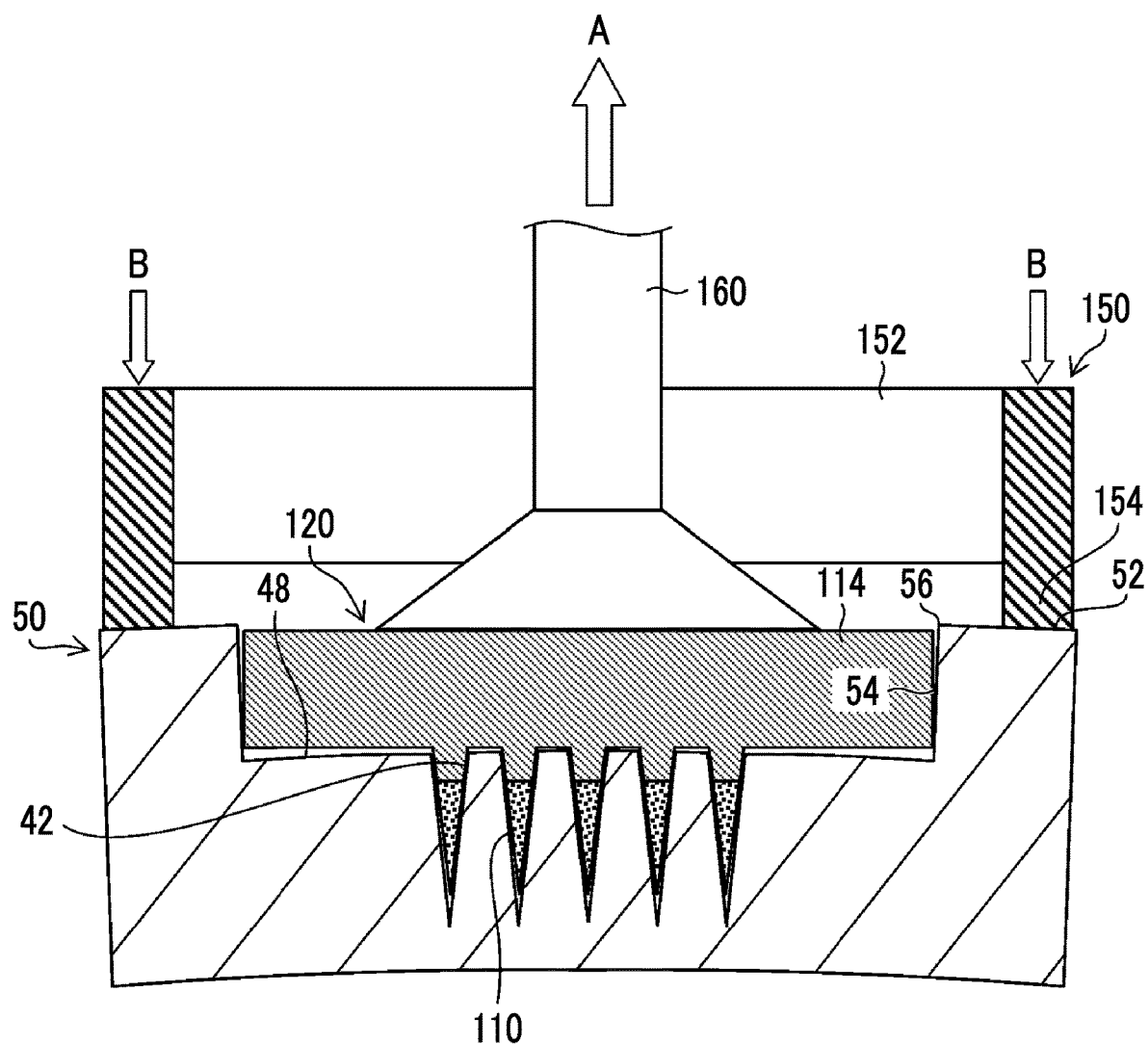
FIG. 14 is a process chart showing the procedure for peeling off a transdermal absorption sheet.

FIG. 14 is a view showing a state where peeling has been started using the vacuum suction pad 160. By pressing force, the end portion of the mold 50 is pressed in a second direction B. Furthermore, the transdermal absorption sheet 120 is aspirated by the vacuum suction pad 160 in a first direction A (a direction opposite to the second direction B) which is a direction perpendicular to the region 48 where the needle-like recess portions 42 are formed. Therefore, the central portion of the mold 50 is pulled by the transdermal absorption sheet 120. Therefore, as shown in FIG. 14, the mold 50 is deformed from the side of the end portion (the side of the wall portion 54) of the region 48 where the needle-like recess portions 42 are formed. As a result, first, the end portion of the transdermal absorption sheet 120 starts to be peeled off from the side of the end portion of the region 48, where the needle-like recess portions 42 are formed, of the mold 50.

Figure 15:
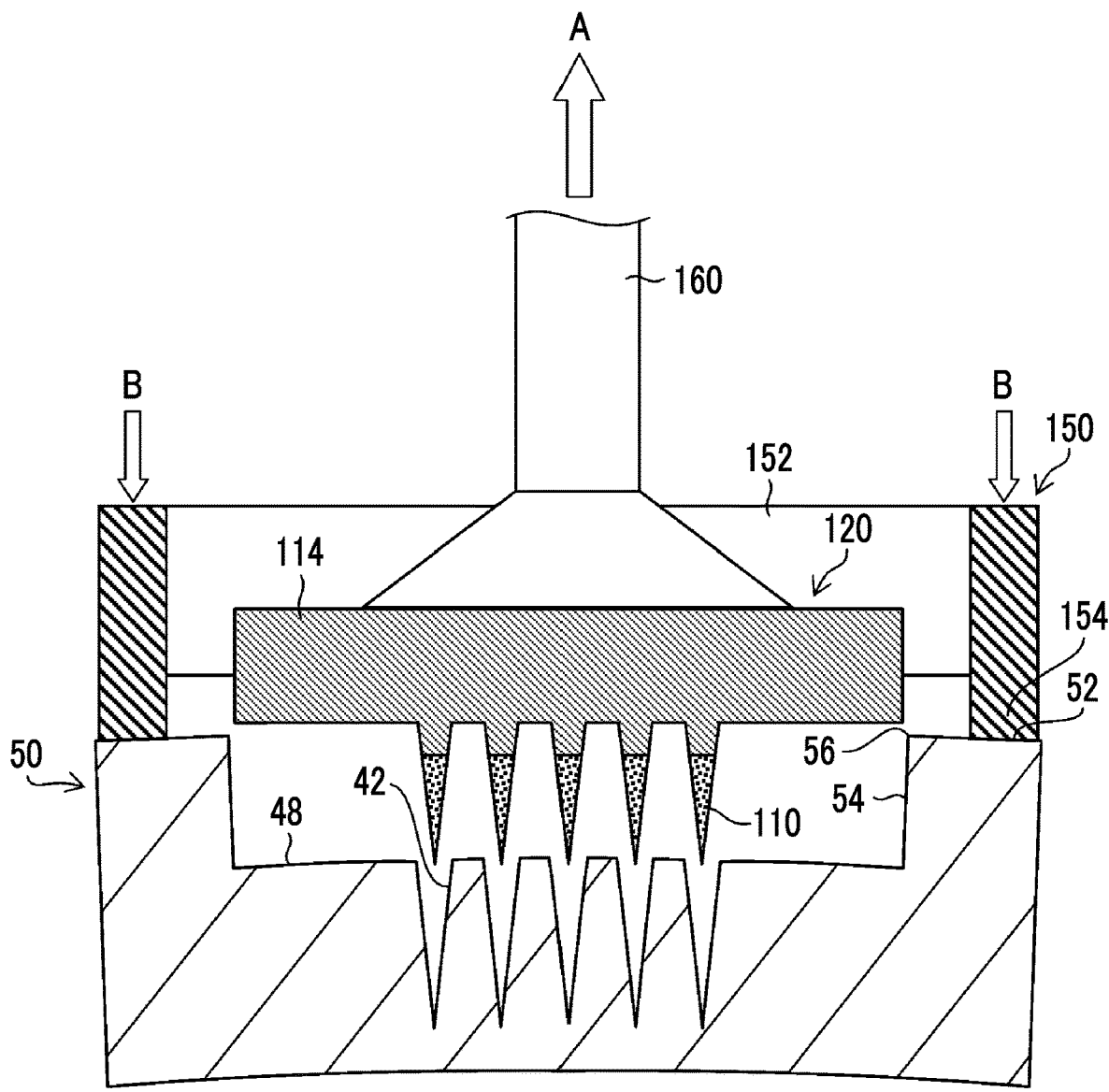
FIG. 15 is a process chart showing the procedure for peeling off a transdermal absorption sheet.

By the vacuum suction pad 160, the transdermal absorption sheet 120 is pulled up in the first direction A. Consequently, the central portion of the mold 50 is further pulled to the transdermal absorption sheet 120. Because the end portion of the mold 50 is pressed by pressing force, the mold 50 is bent. As a result, in the process of releasing and peeling off needle-like protrusion portions 122 of the transdermal absorption sheet 120 from the mold 50, it is possible to inhibit the damage of needle-like protrusion portions 122. Furthermore, by performing aspiration with the vacuum suction pad 160, it is possible to pull up only the transdermal absorption sheet 120 without pulling up the mold 50 together with the transdermal absorption sheet 120 (FIG. 15). In addition, by sufficiently bending the mold 50, it is possible to peel off the transdermal absorption sheet 120 from the mold 50 with low aspiration force. The transdermal absorption sheet 120 can be peeled off by aspiration force equal to or higher than 50 kPa.

The vacuum suction pad 160 is preferably a flat pad. In a case where a flat pad is used, the transdermal absorption sheet 120 can be aspirated in a flat state. Therefore, it is possible to inhibit the transdermal absorption sheet 120 from being deformed during peeling.

Figure 16:
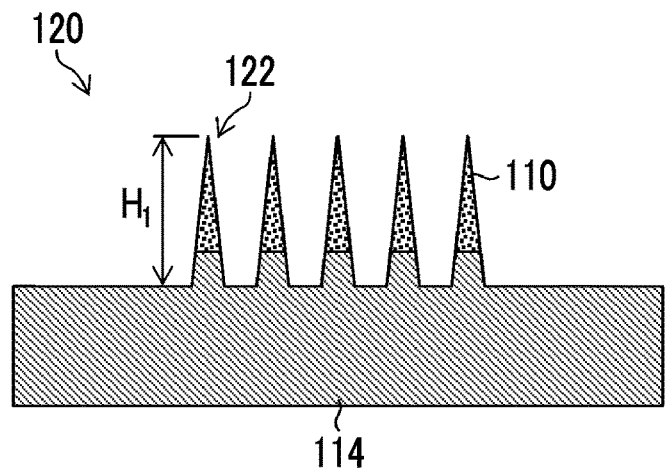
FIG. 16 is a diagram showing a transdermal absorption sheet peeled off.

FIG. 16 is a cross-sectional view showing an example of the transdermal absorption sheet 120 peeled off. The shape of the needle-like protrusion portions 122 of the transdermal absorption sheet 120 to be manufactured is not particularly limited as long as the portions 122 have a tapered tip. For example, the needle-like protrusion portions 122 can be in the form of a cone or in the form of a pyramid such as a trigonal pyramid or a quadrangular pyramid. Furthermore, the needle-like protrusion portions 122 can be formed of a tapered needle portion and a frustum connected to the needle portion.

A height $H_1$ of the needle-like protrusion portions 122 of the protrusion-like pattern is in the range of 100 μm or greater and 2,000 μm or less, preferably 200 μm or greater and 1,500 μm or less.

The transdermal absorption sheet 120 having the needle-like protrusion portions 122 to be manufactured is a replica of the master 10 having the protrusion-like pattern 14. Therefore, by forming the protrusion-like pattern 14 of the master 10 into a desired shape, it is possible to manufacture the transdermal absorption sheet 120 having the needle-like protrusion portions 122 in a desired shape.

[Polymer Layer Forming Solution]

The polymer layer forming solution which is a polymer resin solution used in the present embodiment will be described.

As the material of the resin polymer used in the polymer layer forming solution, it is preferable to use a biocompatible resin. As such a resin, it is preferable to use saccharides such as glucose, maltose, pullulan, chondroitin sulfate, sodium hyaluronate, and hydroxyethyl starch, proteins such as gelatin, and biodegradable polymers such as polylactic acid and a lactic acid/glycolic acid copolymer. Among these, gelatin-based materials exhibit adhesiveness to many substrates and have high gel strength as a gelling material. Therefore, these materials enable the transdermal absorption sheet to be closely attached to the substrate in the process of peeling the transdermal absorption sheet from a mold, and make it easy to peel off the transdermal absorption sheet from the mold by using the substrate. Accordingly, the gelatin-based materials can be suitably used. Although the concentration of the resin polymer varies with the material, the concentration of the resin polymer contained in the polymer layer forming solution is preferably 10% to 50% by mass. As the solvent used for dissolution, in addition to warm water, volatile solvents may also be used. As the solvent, methyl ethyl ketone (MEK), an alcohol, and the like can be used.

In a case where a water-soluble polymer (such as gelatin) is used, the polymer layer forming solution can be prepared by a method of dissolving water-soluble powder in water. In a case where the polymer material is not easily dissolved in water, heating may be performed to dissolve the polymer. Although the temperature can be appropriately selected according to the type of the polymer material, it is preferable to heat the polymer material at about a temperature equal to or lower than 60° C. The viscosity of the polymer layer forming solution is preferably equal to or lower than 2,000 Pa·s, and more preferably equal to or lower than 1,000 Pa·s. By appropriately adjusting the viscosity of the polymer layer forming solution, the polymer layer forming solution can be easily injected into the needle-like recess portions of the mold. The viscosity of the polymer layer forming solution can be measured, for example, by a capillary viscometer, a falling ball viscometer, a rotary viscometer, or a vibrating viscometer.

[Drug Solution]

The drug solution forming the drug layer 110 will be described. The drug solution is a solution containing a predetermined amount of a drug in the polymer layer forming solution. Whether or not the drug solution contains a predetermined amount of a drug is determined by whether or not the drug solution can exert efficacy in a case where the drug solution penetrates into the body surface. Therefore, containing a predetermined amount of a drug means that the drug solution contains a drug in such an amount that exerts efficacy in a case where the drug solution penetrates into the body surface.

The drug to be incorporated into the drug solution is not limited as long as it functions as a drug. Particularly, it is preferable to select the drug from peptides, proteins, nucleic acids, polysaccharides, vaccines, pharmaceutical compounds belonging to water-soluble low molecular weight compounds, or cosmetic ingredients.

The concentration of polymers contained in the drug solution (the concentration of polymers excluding a drug in a case where the drug is a polymer) is preferably 0% to 30% by mass. Furthermore, the viscosity of the drug solution is preferably equal to or lower than 100 Pa·s, and more preferably equal to or lower than 10 Pa·s.

EXAMPLES

Hereinafter, the present invention will be more specifically described with reference to examples of the present invention. The materials, the amount of the materials used, the proportion of the materials, the details of treatments, the treatment procedures, and the like that will be described in the following examples can be appropriately modified as long as the gist of the present invention is maintained. Therefore, the scope of the present invention is not limited to the following specific examples.

As a mold, a circular silicone rubber mold (made of SIL-5930) having a diameter of 20 mm and 121 needle-like recess portions was used. The step portion had a width of 2 mm, and the diameter of the inside of the step portion (diameter of a region where needle-like recess portions were formed) was 16 mm. Furthermore, the depth of the step portion (distance between the step portion and the region where the needle-like recess portions were formed) was 0.5 mm.

A 40 wt % aqueous chondroitin sulfate (CS) solution (250 mg) was added dropwise to the inside of the step portion of the mold and dried, thereby manufacturing a transdermal absorption sheet. The transdermal absorption sheet manufactured in the present example was prepared to check the release properties in the step of peeling off. Therefore, only the polymer layer forming solution was used to manufacture the transdermal absorption sheet, and no drug layer was formed. The moisture content in the manufactured transdermal absorption sheet was 18 wt %. The pressing jig shown in FIG. 12 was placed on the step portion on the outer periphery of the mold, and pressed on the mold so that pressing force was applied. The pressing jig had an outer diameter of 20 mm and an inner diameter of 18 mm, and included claw portions having a height of 2 mm. Furthermore, the claw portions each had a length of 5 mm in the circumferential direction, and were arranged on the circumference at equal intervals. In addition to the pressing jig shown in FIG. 11 having two claw portions, pressing jigs provided with 3 or 4 claw portions were also tested for release properties. In the pressing jigs provided with 3 or 4 claw portions, the claw portions each had a length of 5 mm in the circumferential direction and were arranged on the circumference at equal intervals. In a state where the pressing force was being applied to the mold by the pressing jig, a vacuum suction pad (flat pad) was brought into contact with the back surface side of the transdermal absorption sheet, and the transdermal absorption sheet was pulled up with an aspiration force of 50 to 60 kPa.

As a comparative example, a transdermal absorption sheet was manufactured in the same manner as in the above example by using a 40 wt % aqueous chondroitin sulfate solution. The entire circumference of the step portion of the mold was pressed so that the mold was fixed to the mold installation surface. In this state, a vacuum suction pad was brought into contact with the back surface side of the transdermal absorption sheet, and the transdermal absorption sheet was pulled up with an aspiration force of 98 kPa. The release properties were evaluated based on the following standard.

A: The transdermal absorption sheet could be peeled off from the mold without damaging the needle-like protrusion portions.

B: Although the needle-like protrusion portions were damaged during peeling, the damage was unproblematic for the transdermal absorption sheet to be used.

C: The transdermal absorption sheet could not be peeled off.

The results are shown in Table 1.

TABLE 1

| | Step portion pressing position | Suction pad Vacuum aspiration force | Evaluation of release properties |
| --- | --- | --- | --- |
| Example 1 | Two sites (each having width of about 5 mm) on circumference at equal intervals | 50 to 60 kPa | A |
| Example 2 | Three sites (each having width of about 5 mm) on circumference at equal intervals | 50 to 60 kPa | A |
| Example 3 | Four sites (each having width of about 5 mm) on circumference at equal intervals | 50 to 60 kPa | B |
| Comparative Example 1 | Entire circumference | 98 kPa | C |

In Examples 1 and 2 in which pressing force was applied to the mold at 2 sites or 3 sites on the step portion, the transdermal absorption sheet could be peeled off without deforming the needle-like protrusion portions. Even in Example 3 in which pressing force was applied to the mold at 4 sites on the step portion, the manufactured transdermal absorption sheet had no problem for use.

In Comparative Example 1 in which the entire circumference of the step portion of the mold was pressed to apply pressing force, the mold was not deformed. Furthermore, even though the transdermal absorption sheet was aspirated with an aspiration force higher than the aspiration force in Examples 1 to 3, and the vacuum suction pad was pulled up, the transdermal absorption sheet could not be peeled off. In the present example, the transdermal absorption sheet could be peeled off with an aspiration force lower than the aspiration force in the comparative example.

According to the method for manufacturing a transdermal absorption sheet of an embodiment of the present invention, even though pressing force is not applied to the entire circumference of a mold, the mold can be deformed by pressing force by the application of the pressing force to a part of the circumference of the mold. In addition, because the pressing force acts in a direction opposite to a direction in which the transdermal absorption sheet is peeled off from the mold, by performing aspiration with a vacuum suction pad, it is possible to bend the mold and to easily peel off the needle-like protrusion portions from the mold. Therefore, by peeling the transdermal absorption sheet in the direction perpendicular to the region where the needle-like recess portions are formed, it is possible to manufacture a transdermal absorption sheet without damaging the needle-like protrusion portions of the transdermal absorption sheet.

EXPLANATION OF REFERENCES

10: master
12, 32: needle-like protrusion portion
14, 34: protrusion-like pattern
20: first mold
22, 42: needle-like recess portions
24, 44: recess-like pattern
30: replication mold
40: mold sheet
48: region where needle-like recess portions are formed
50: mold
52: step portion
54: wall portion
56: contact position
90: supply unit
110: drug layer
112: polymer layer forming solution
114: polymer layer
120: transdermal absorption sheet
122: needle-like protrusion portion
150: pressing jig
152: base portion
154: claw portion
160: vacuum suction pad
A: first direction
B: second direction

What is claimed is:

1. A method for manufacturing a transdermal absorption sheet, comprising:

a step of filling needle-like recess portions of a mold with a drug solution and drying the drug solution so as to form a drug layer, wherein the mold includes the needle-like recess portions and a step portion that is formed around a region where the needle-like recess portions are formed, and an upper surface of the step portion is higher than an upper surface of the region where the needle-like recess portions are formed;

a step of supplying a polymer layer forming solution to an inside of the step portion;

a step of drying the polymer layer forming solution so as to form a polymer layer and a transdermal absorption sheet; and a step of peeling off the transdermal absorption sheet from the mold, wherein in the step of peeling off, pressing force is applied to a part of the step portion in a second direction opposite to a first direction in which the transdermal absorption sheet is released from the mold, and the transdermal absorption sheet is aspirated by a vacuum suction pad from a side opposite to the mold so that the transdermal absorption sheet is peeled off from the mold in the first direction, and wherein the pressing force is applied using a pressing jig, and in an entire circumference of the step portion of the mold, a proportion of the part to which the pressing force is applied is equal to or lower than 75%.

2. The method for manufacturing a transdermal absorption sheet according to claim 1,
wherein the vacuum suction pad is a flat pad.

3. The method for manufacturing a transdermal absorption sheet according to claim 1,
wherein the pressing force is applied to the step portion at equal intervals.

4. The method for manufacturing a transdermal absorption sheet according to claim 1,
wherein in a case where a point of contact between the step portion and a wall portion extending to the step portion from the region where the needle-like recess portions are formed is regarded as a contact position, in the step of supplying the polymer layer forming solution, the polymer layer forming solution is supplied so that the solution flows over the contact position from the region where the needle-like recess portions are formed and is then fixed to the contact position while being contracted.

5. The method for manufacturing a transdermal absorption sheet according to claim 1,
wherein the first direction is a direction perpendicular to the region where the needle-like recess portions are formed.

6. The method for manufacturing a transdermal absorption sheet according to claim 1,
wherein an aspiration force of the vacuum suction pad is equal to or higher than 50 kPa and equal to or lower than 60 kPa.

7. The method for manufacturing a transdermal absorption sheet according to claim 1,
wherein the pressing force is applied using the pressing jig including a tubular base portion and claw portions connected to the base portion by bringing the claw portions into contact with the step portion.

* * * * *